United States Patent [19]

Patel

[11] 4,187,098

[45] Feb. 5, 1980

[54] SELECTIVELY HERBICIDAL N-(5-SUBSTITUTED-2-THIADIAZOLYL)-THIOCARBOXAMIDES

[75] Inventor: Natu R. Patel, Overland Park, Kans.

[73] Assignee: Gulf Oil Corporation, Pittsburgh, Pa.

[21] Appl. No.: 963,553

[22] Filed: Nov. 24, 1978

[51] Int. Cl.$^2$ ............................................. A01N 9/12
[52] U.S. Cl. ...................................... 71/90; 548/139
[58] Field of Search ................... 71/90; 260/306.8 D

[56] References Cited

U.S. PATENT DOCUMENTS

| | | | |
|---|---|---|---|
| 3,824,247 | 7/1974 | Doyle, Jr. et al. ...................... | 71/90 |
| 3,990,879 | 11/1976 | Soper ....................................... | 71/90 |
| 4,092,148 | 5/1978 | Cebalo ..................................... | 71/90 |
| 4,097,263 | 6/1978 | Kirkpatrick ............................. | 71/90 |

FOREIGN PATENT DOCUMENTS 743614  6/1970  Belgium ........................................ 71/90

OTHER PUBLICATIONS

Skiles et al, "Herbicidal Thiadiazoles," CA 80 No. 37115u, (1973).

*Primary Examiner*—Glennon H. Hollrah
*Attorney, Agent, or Firm*—Carl A. Cline

[57] ABSTRACT

A group of 5-substituted-2-thiadiazolyl thiocarboxamides is useful as selective herbicides, particularly in combating weeds in grain crops. The herbicidal properties of the compounds are superior to those of corresponding carboxamides.

8 Claims, No Drawings

SELECTIVELY HERBICIDAL N-(5-SUBSTITUTED-2-THIADIAZOLYL)-THIOCARBOXAMIDES

DESCRIPTION OF THE INVENTION

In U.S. Pat. No. 3,823,005 there is disclosed a small class of N-(chloro-tert-butylthiadiazolyl)carboxamides which are effective as herbicides against many weed species. There are many N-thiadiazolylcarboxamides, however, that are relatively ineffective as herbicides and in some instances also have poor selectivity, so that they have little or no practical utility. I have discovered a group of N-thiadiazolylthiocarboxamides which are superior to the corresponding carboxamides, possessing improved efficacy, particularly with regard to cocklebur, morning glory, barnyard grass and green foxtail. These new herbicides are particularly useful in selectively combating unwanted vegetation in the presence of peanuts, corn (Zea mays) and small grains.

Briefly, the novel selective herbicides of this invention are compounds of the general structural formula

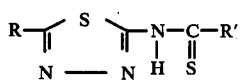

in which R is trifluoromethyl, N,N-dimethylsulfamyl or N,N-diethylsulfamyl and R' is ethyl or isopropyl. The synthesis of these compounds has been achieved by known methods, employing available intermediates eq (1). R. B. Wagner and H. D. Zook, "Synthetic Organic Chemistry", John Wiley and Sons, N.Y., 1953, p. 827.

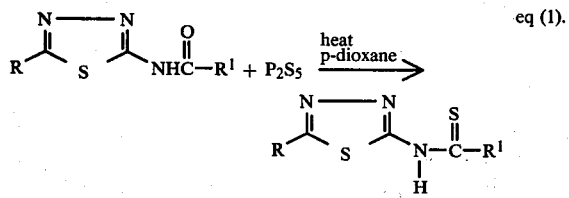

eq (1).

The following procedure illustrates the synthesis.

Preparation of 2-diethylsulfamyl-5-propylthiocarboxamido-1,3,4-thiadiazole.

To 125 ml of dry p-dioxane 7.9 g (0.027 m) 2-diethylsulfamoyl-5-propylcarboxamido-1,3,4-thiadiazole, and 6.7 g (0.03 m) phosphorus pentasulfide is added. The mixture is stirred and refluxed under argon for three hours to give almost clear solution. Cool to room temperature and filter into 500 ml of stirring water. Let it stir overnight, filter wash with water and dry to give 7.0 g yellowish powder.

Recrystallized from toluene, 5.3 g (63%) yellow needles m.p. 197°–99°.

Below are listed compounds of the above general structural formula which have been synthesized by means of the above illustrative procedure:

| Compound No. | R | R' | m.p. (deg.C.) |
|---|---|---|---|
| 1 | —CF$_3$ | —C$_2$H$_5$ | 197°–200° |
| 2 | —CF$_3$ | —CH(CH$_3$)$_2$ | 156°–158° |
| 3 | —SO$_2$N(CH$_3$)$_2$ | —C$_2$H$_5$ | 214°–216° |
| 4 | —SO$_2$N(CH$_3$)$_2$ | —CH(CH$_3$)$_2$ | 199°–201° |
| 5 | —SO$_2$N(C$_2$H$_5$)$_2$ | —CH(CH$_3$)$_2$ | 158°–161° |

Combating Unwanted Vegetation

The novel herbicides are effective when used both post- and pre-emergently. There is described below an illustrative procedure for herbicidal use of the compounds under controlled conditions in the greenhouse so as to obtain data on phytotoxic activity and selectivity.

(1) Post-Emergent Use

An aqueous dispersion of each active compound was prepared by combining 0.4 gram of the compound with about 4 ml of a solvent-emulsifier mixture (3 parts of a commercial polyoxyethylated vegetable oil emulsifier, one part xylene, one part kerosene) and then adding water, with stirring, to a final volume of 40 ml.

The 24 species of plants on which each compound was to be tested were planted in disposable plastic pots in a greenhouse. Ten to eighteen days after emergence of the plants, three pots of each species were sprayed at each rate with an aqueous dispersion of the active compound prepared as described above, at rates of both 1 lb and 3 lb of active compound per acre and at a spray volume of 60 gallons per acre. Approximately one week after the spray application the plants were observed and the results rated according to the following schedule.

DEGREE OF EFFECT

0=no effect

1=slight effect, plants recovered

2=moderate effect, injury to 26 to 75 percent of foliage

3=severe effect, injury to 76 to 99 percent of foliage

4=maximum effect (all plants died)

The same rating schedule was employed to judge pre-emergent results obtained according to the procedure below.

(2) Pre-Emergent Use

A solution of each active compound was prepared by dissolving 290 mg of the compound to be tested in 200 ml of acetone. Disposable paper trays about 2 ½ inches deep were filled with soil and sprayed with the acetone solution at rates of 3 lb and 1 lb of active chemical per acre of sprayed area, were seeded with 24 species of plant seeds and were then covered with about ¼ inch of soil. Twenty-one days after seeding and treatment the plantings were examined and herbicidal effect was rated.

Results are summarized in the following table.

| PLANT SPECIES | Appl'n. Rate (lb./A) | Compound No. 1 Pre | 1 Post | 2 Pre | 2 Post | 3 Pre | 3 Post | 4 Pre | 4 Post | 5 Pre | 5 Post |
|---|---|---|---|---|---|---|---|---|---|---|---|
| Xanthium pensylvanicum | 3 | 0 | 4 | | 4 | 2 | 4 | | 4 | 1 | 4 |
| Cocklebur | 1 | 0 | 4 | 0 | 4 | 1 | 4 | 0 | 4 | 0 | 4 |
| Chenopodium allum | 3 | 4 | 4 | | 4 | 4 | 4 | | 4 | 4 | 4 |
| Lambsquarters | 1 | 3 | 4 | 4 | 4 | 4 | 4 | 3 | 4 | 4 | 4 |

-continued

| PLANT SPECIES | Appl'n. Rate (lb./A) | Compound No. | | | | | | | | | |
|---|---|---|---|---|---|---|---|---|---|---|---|
| | | 1 | | 2 | | 3 | | 4 | | 5 | |
| | | Pre | Post | Pre | Post | Pre | Post | Pre | Post | Pre | Post |
| *Ipomoea purpurea* | 3 | 1 | 4 | | 4 | 4 | 4 | | 4 | 4 | 4 |
| Morning Glory | 1 | 0 | 4 | 0 | 3 | 2 | 4 | 0 | 1 | 1 | 2 |
| *Amaranthus retroflexus* | 3 | 4 | 4 | | 4 | 4 | 4 | | 4 | 4 | 4 |
| Pigweed | 1 | 4 | 4 | 3 | 4 | 4 | 3 | 4 | 4 | 1 | 1 |
| *Polygonum convolvulus* | 3 | 4 | 4 | | 4 | 4 | 4 | | 4 | 4 | 4 |
| Wild Buckwheat | 1 | 1 | 4 | 1 | 4 | 4 | 4 | 0 | 4 | 2 | 2 |
| *Brassica kaber* | 3 | 4 | 4 | | 4 | 4 | 4 | | 4 | 3 | 4 |
| Wild Mustard | 1 | 4 | 4 | 2 | 4 | 4 | 4 | 0 | 4 | 2 | 4 |
| *Echinochloa crusgalli* | 3 | 2 | 4 | | 4 | 4 | 4 | | 4 | 2 | 3 |
| Barnyard grass | 1 | 0 | 2 | 0 | 2 | 3 | 4 | 1 | 4 | 1 | 1 |
| *Digitaria sanguinalis* | 3 | 1 | 3 | | 3 | 4 | 4 | | 2 | 0 | 1 |
| Crabgrass | 1 | 0 | 0 | 0 | 3 | 3 | 1 | 3 | 0 | 0 | 0 |
| *Bromus tectorum* | 3 | 0 | 3 | | 4 | 3 | 3 | | 2 | 0 | 2 |
| Downy Brome | 1 | 0 | 0 | 0 | 4 | 1 | 2 | 0 | 1 | 0 | 0 |
| *Setaria faberii* | 3 | 1 | 2 | | 4 | 4 | 4 | | 2 | 0 | 1 |
| Giant Foxtail | 1 | 0 | 0 | 0 | 1 | 2 | 4 | 1 | 1 | 0 | 0 |
| *Setaria viridis* | 3 | 2 | 4 | | 4 | 4 | 4 | | 4 | 1 | 3 |
| Green Foxtail | 1 | 0 | 4 | 1 | 4 | 2 | 4 | 0 | 4 | 1 | 1 |
| *Cyperus esculentis* | 3 | 0 | 0 | | 1 | 0 | 1 | | 0 | 0 | 0 |
| Nutsedge | 1 | 0 | 0 | 0 | 0 | 0 | 0 | 0 | 0 | 0 | 0 |
| *Sorghum bicolor* | 3 | 0 | 4 | | 4 | 4 | 4 | | 3 | 1 | 2 |
| Shatter Cane | 1 | 0 | 1 | 0 | 1 | 2 | 1 | 0 | 1 | 0 | 0 |
| *Avena fatua* | 3 | 1 | 2 | | 4 | 4 | 4 | | 4 | 0 | 1 |
| Wild Oats | 1 | 0 | 0 | 0 | 2 | 1 | 1 | 0 | 2 | 0 | 0 |
| *Medicago sativa* | 3 | 3 | 4 | | 4 | 1 | 4 | | 4 | 4 | 3 |
| Alfalfa | 1 | 1 | 4 | 1 | 4 | 0 | 3 | 0 | 4 | 1 | 1 |
| *Gossypium herbaceum* | 3 | 1 | 4 | | 4 | 3 | 4 | | 4 | 0 | 2 |
| Cotton | 1 | 0 | 3 | 0 | 4 | 1 | 4 | 0 | 4 | 1 | 1 |
| *Arachis hypogaca* | 3 | 0 | 1 | | 2 | 0 | 3 | | 1 | 0 | 0 |
| Peanut | 1 | 0 | 0 | 0 | 1 | 0 | 2 | 0 | 1 | 0 | 0 |
| *Soja max* | 3 | 1 | 4 | | 4 | 2 | 4 | | 3 | 4 | 3 |
| Soybean | 1 | 0 | 3 | 0 | 1 | 1 | 4 | 0 | 1 | 4 | 1 |
| *Beta vulgaris* | 3 | 4 | 4 | | 4 | 4 | 4 | | 4 | 1 | 4 |
| Sugar Beets | 1 | 4 | 3 | 1 | 4 | 3 | 4 | 1 | 4 | 1 | 2 |
| *Lycopersicum esculentum* | 3 | 2 | 4 | | 4 | 3 | 4 | | 4 | 1 | 0 |
| Tomato | 1 | 1 | 4 | 1 | 4 | 2 | 3 | 1 | 3 | 4 | 3 |
| *Zea mays* | 3 | 0 | 2 | | 3 | 3 | 2 | | 1 | 0 | 1 |
| Corn | 1 | 0 | 0 | 0 | 1 | 2 | 0 | 0 | 0 | 0 | 0 |
| *Sorghum vulgare* | 3 | 0 | 3 | | 3 | 4 | 4 | | 2 | 0 | 2 |
| Grain Sorghum | 1 | 0 | 1 | 0 | 1 | 2 | 1 | 0 | 1 | 0 | 0 |
| *Oryna sativa* | 3 | 0 | 3 | | 4 | 4 | 4 | | 4 | 1 | 2 |
| Rice | 1 | 0 | 0 | 0 | 2 | 2 | 2 | 0 | 1 | 0 | 0 |
| *Triticum aestivum* | 3 | 1 | 2 | | 4 | 2 | 4 | | 4 | 0 | 2 |
| Wheat | 1 | 0 | 0 | 0 | 3 | 0 | 1 | 0 | 1 | 0 | 0 |

Of the compounds exemplified above, compound No. 3 is particularly effective, both pre- and post-emergently in combating unwanted vegetation. All of the exemplified thiocarboxamido compounds exhibit unexpectedly superior herbicidal properties in comparison with the carboxamido compounds from which they were made. In general, improved efficacy against such weeds as barnyard grass, greenfoxtail morning glory and cocklebur appears to result from the presence of sulfur, rather than oxygen in these herbicides.

I claim:

1. The selectively herbicidal composition which comprises an effective amount of a compound which has the general structural formula

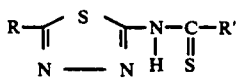

in which R is trifluoromethyl, N,N-dimethylsulfamyl, or N,N-diethylsulfamyl and R' is ethyl or isopropyl in combination with an inert carrier.

2. The composition according to claim 1 in which R is trifluoromethyl and R' is ethyl.

3. The composition according to claim 1 in which R is trifluoromethyl and R' is isopropyl.

4. The composition according to claim 1 in which R is N,N-dimethylsulfamyl and R' is ethyl.

5. The composition according to claim 1 in which R is N,N-dimethylsulfamyl and R' is isopropyl.

6. The composition according to claim 1 in which R is N,N-diethylsulfamyl and R' is isopropyl.

7. The method of combating unwanted vegetation comprising applying either pre- or post-emergently to the locus of the vegetation an effective amount of a compound which has the general structural formula

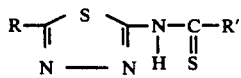

in which R is trifluoromethyl, N,N-dimethylsulfamyl, or N,N-diethylsulfamyl and R' is ethyl or isopropyl in combination with an inert carrier.

8. The method according to claim 7 in which R is N,N-dimethylsulfamyl and R' is ethyl.

* * * * *

UNITED STATES PATENT OFFICE
CERTIFICATE OF CORRECTION

Patent No. 4,187,098  Dated February 5, 1980

Inventor(s) Natu R. Patel

It is certified that error appears in the above-identified patent and that said Letters Patent are hereby corrected as shown below:

Column 1, line 47, should read 2-diethylsulfamyl-5-"ethylthiocarboxamido"-1,3,4-

Column 1, line 51, should read sulfamoyl-5-"ethylcarboxamido"-1,3,4-thiadiazole, and Signed and Sealed this Twenty-sixth Day of August 1980

[SEAL]

Attest:

SIDNEY A. DIAMOND

Attesting Officer   Commissioner of Patents and Trademarks